United States Patent [19]

Kinson et al.

[11] 4,073,814
[45] Feb. 14, 1978

[54] DEHYDROCHLORINATION METHOD

[75] Inventors: Philip L. Kinson, Clifton Park, N.Y.; Clayton B. Quinn, Mount Vernon, Ind.

[73] Assignee: General Electric Company, Schenectady, N.Y.

[21] Appl. No.: 768,209

[22] Filed: Feb. 14, 1977

[51] Int. Cl.$^2$ ............................................. C07C 37/00
[52] U.S. Cl. ........................... 260/619 A; 260/520 R; 260/590 D; 260/619 B; 560/57
[58] Field of Search ................................. 260/619 A

[56] References Cited

U.S. PATENT DOCUMENTS 3,856,556  12/1974  Bzozowski et al. ............. 260/619 A

*Primary Examiner*—Norman Morganstern
*Attorney, Agent, or Firm*—William A. Teoli; Joseph T. Cohen; Jerome C. Squillaro

[57] ABSTRACT

A method is provided for dehydrochlorinating 1,1,1-trichloro-2,2-bis(4-hydroxyphenyl)ethane to produce substantially pure 1,1-dichloro-2,2-bis(4-hydroxyphenyl)ethylene, based on the employment of a dipolar aprotic solvent and a basic alkali metal compound, such as sodium hydroxide, sodium carbonate, etc. Crystallization of the 1,1-bis(p-hydroxyphenyl)-2,2-dichloroethylene from the dehydrochlorination reaction mixture can provide monomer useful for making high impact, flame retardant thermoplastic polycarbonates.

10 Claims, 3 Drawing Figures

DEHYDROCHLORINATION METHOD

The present invention relates to a dehydrochlorination method based on the use of a basic alkali metal compound and a dipolar aprotic solvent. More particularly, the present invention relates to the dehydrochlorination of 1,1,1-trichloro-2,2-bis(4-hydroxyphenyl)ethane to produce substantially pure 1,1-dichloro-2,2-bis(4-hydroxyphenyl)ethylene.

As taught by S. Porejko and Z. Weilgosz, Synthesis and Properties of Polycarbonates with Chlorobisphenols, Polymeri 13 (2), 55 (1968),1,1-dichloro-2,2-bis(4-hydroxyphenyl)ethylene, of the formula,

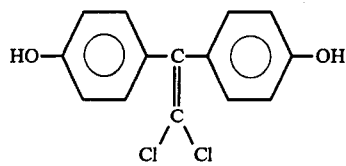

(1)

hereinafter referred to as the "dichloride", can be used to make high molecular weight polycarbonates. The procedure recommended by Porejko et al for making the dichloride is based on the dehydrochlorination of the corresponding 1,1,1-trichloro-2,2-bis(4-hydroxyphenyl)ethane, as shown by the following equation

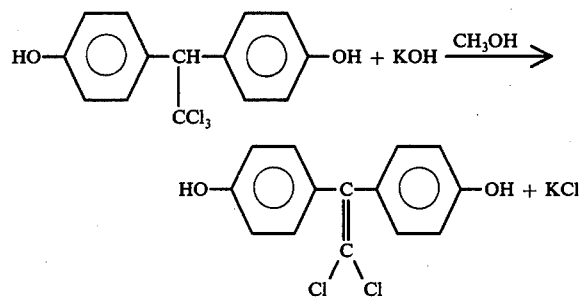

Experience has shown that although the dehydrochlorination of 1,1,1-trichloro-2,2-bis(4-hydroxyphenyl)ethane, hereinafter referred to as the "trichloride", based on the use of a methanol solution of potassium hydroxide, can be employed to produce the dichloride, the yields are often less than satisfactory.

It has been found, for example, a high degree of rearrangement can occur during the formation of the dichloride. The resulting dehydrochlorination reaction solids can contain the dichloride of formula (1), unreacted trichloride of the formula,

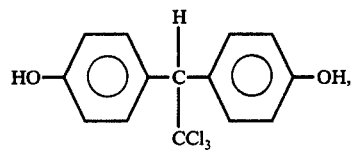

(2)

and one or more of the following by-products:

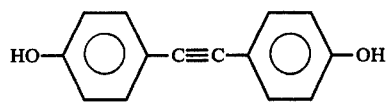

(3)

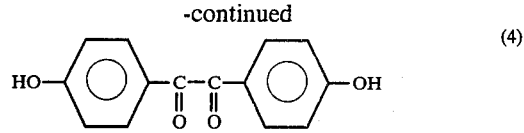

(4)

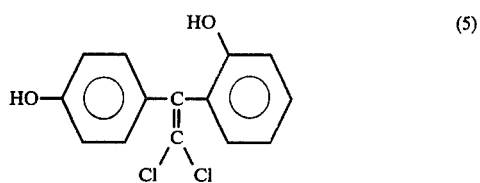

(5)

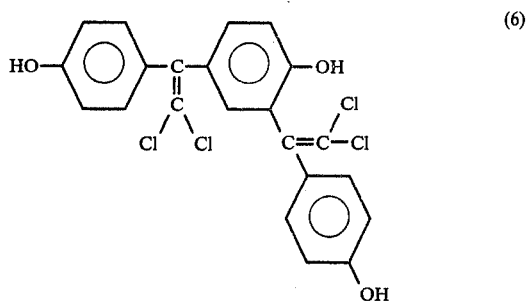

(6)

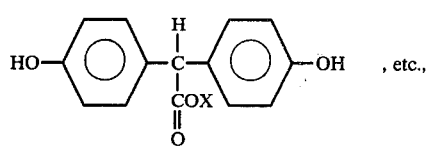

(7)

where X is selected from H and methyl.

Figure 1:
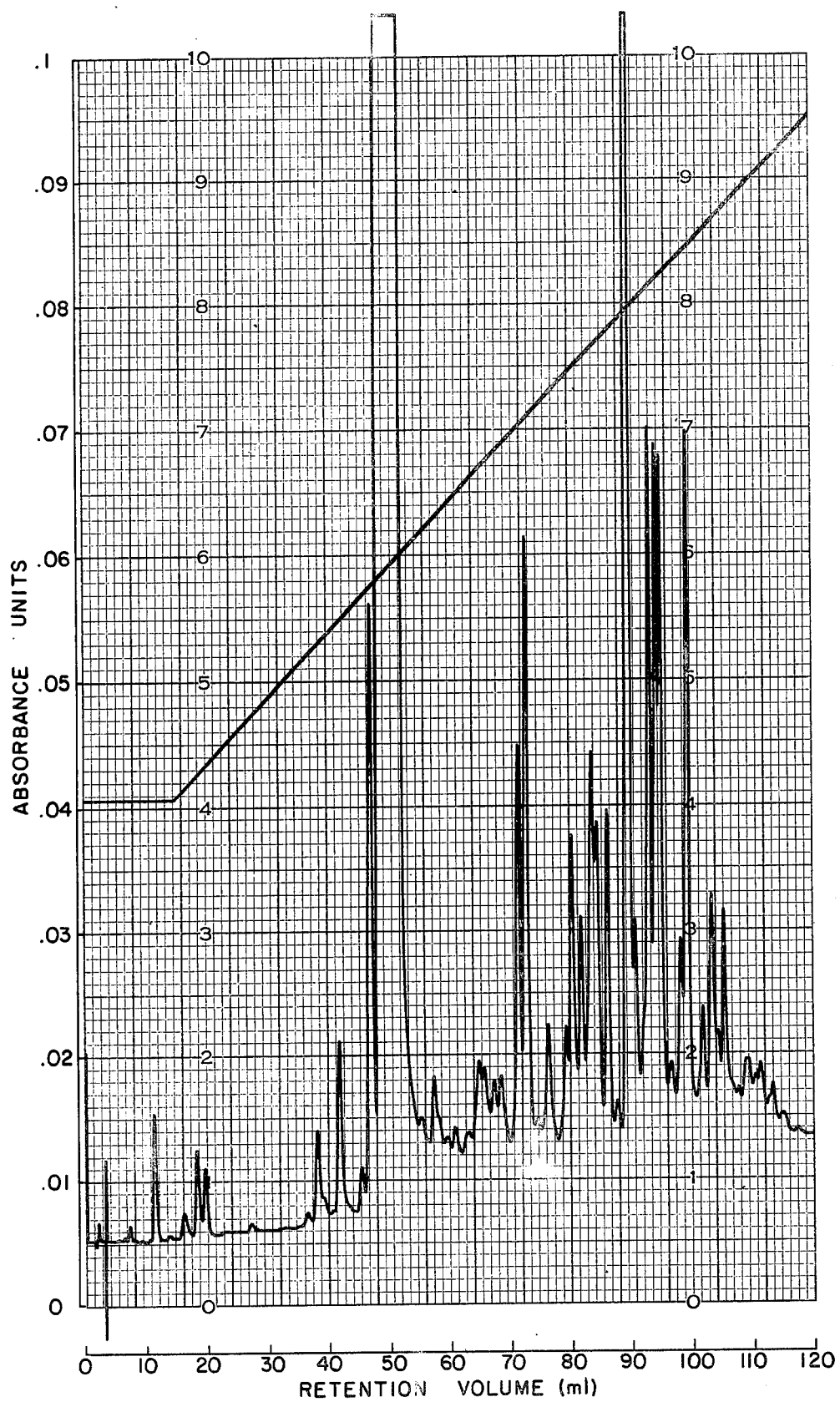

FIG. 1 is a typical liquid chromatogram of the above described dehydrochlorination mixture of Porejko et al. Dichloride absorbance is shown at about 50 ml Retention Volume. The absorbances of contaminants are also shown.

Figure 2:
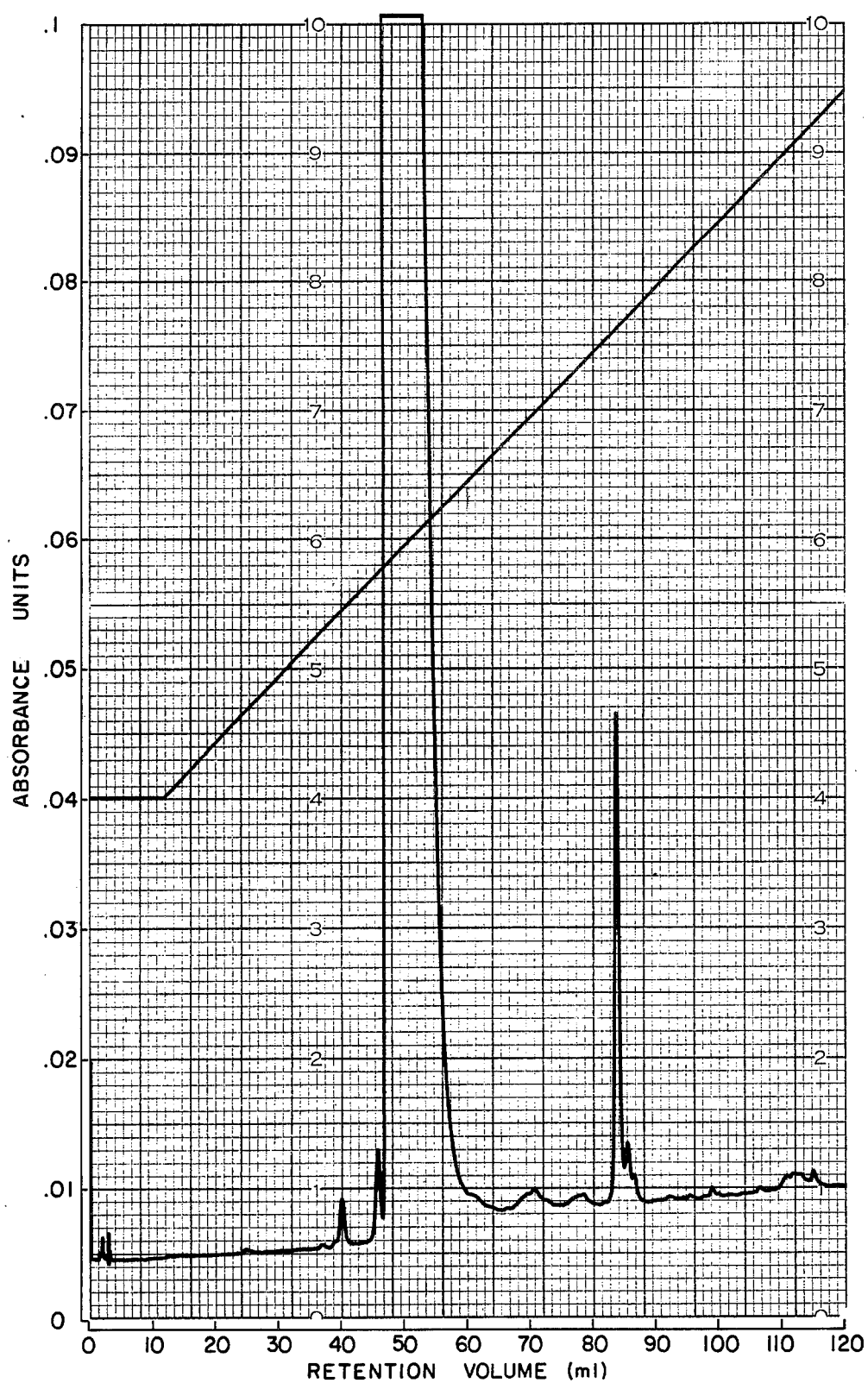

FIG. 2 is a liquid chromatogram of dichloride made by the method of Cleveland et al., copending application Ser. No. 765,654, assigned to the same assignee as the present invention. As shown by FIG. 2, there are no absorbances other than the dichloride exceeding 50% of full scale. The Cleveland et al. method is based on the use of a lithium halide catalyst in a refluxing dipolar aprotic solvent as the dehydrochlorination reaction medium. The resulting dichloride is also substantially color-free as shown by an absorbance of less than 0.3 using a Carey 14 spectrophotometer in accordance with a color determination procedure defined below. The dichloride of Cleveland et al. also can be converted to high impact polycarbonate by standard phosgenation technique. However, Cleveland et al.'s method suffers from an acidic reaction mixture based on the generation of hydrogen chloride during dehydrochlorination and the absence of a neutralizing base. As a result, decomposition of the dipolar aprotic solvent occurs, rendering the Cleveland et al. procedure less economically attractive.

The present invention is based on the discovery that dehydrochlorination of the trichloride of formula (2) can be achieved with a mixture of the trichloride and dipolar aprotic solvent containing as little as 1.1 moles or molar equivalents of alkali metal of certain basic alkali metal compounds, such as sodium hydroxide, sodium carbonate, sodium bicarbonate, potassium carbonate, potassium phosphate, potassium bicarbonate, etc. Essentially quantitative conversions of the trichloride of formula (2) to the dichloride of formula (1) can be achieved. In addition, the resulting dichloride is also substantially free of contamination as shown by the liquid chromatogram of FIG. 3. Considerably less base, per mole of trichloride is required in the method of the present invention to achieve effective dehydrochlorination compared to the 15 moles of KOH per mole of trichloride taught above by Porejko et al, or the 4–8 moles of KOH per mole of trichloride of Wielgosz et al, Polish Pat. No. 144,756.

There is provided by the present invention, a method for making the dichloride of formula (1) by dehydrochlorinating the trichloride of formula (2), which comprises, (1) heating to a temperature in the range of 40° C to 120° C, a mixture containing as essential ingredients,
(a) the trichloride of formula (2)
(b) a dipolar aprotic solvent,
(c) a basic halide-free alkali metal compound selected from sodium compounds and potassium compounds, where, per 100 parts by weight of (b), there is present from 5 to 100 parts of (a), and per mole of (a), there is present at least 1.1 moles or molar equivalents of alkali metal of (c), (2) adding water and a member selected from the class consisting of organic acid and mineral acid to the mixture of (1) in amounts sufficient to produce a mixture having a pH less than about 8 and comprising from 0.8 to 2 parts of water per part of dipolar aprotic solvent, (3) effecting the crystallization of dichloride crystals from the mixture of (2) at a temperature of from about 35° C to 100° C, and (4) recovering the crystalline dichloride from the resulting mixture of (3).

Figure 3:
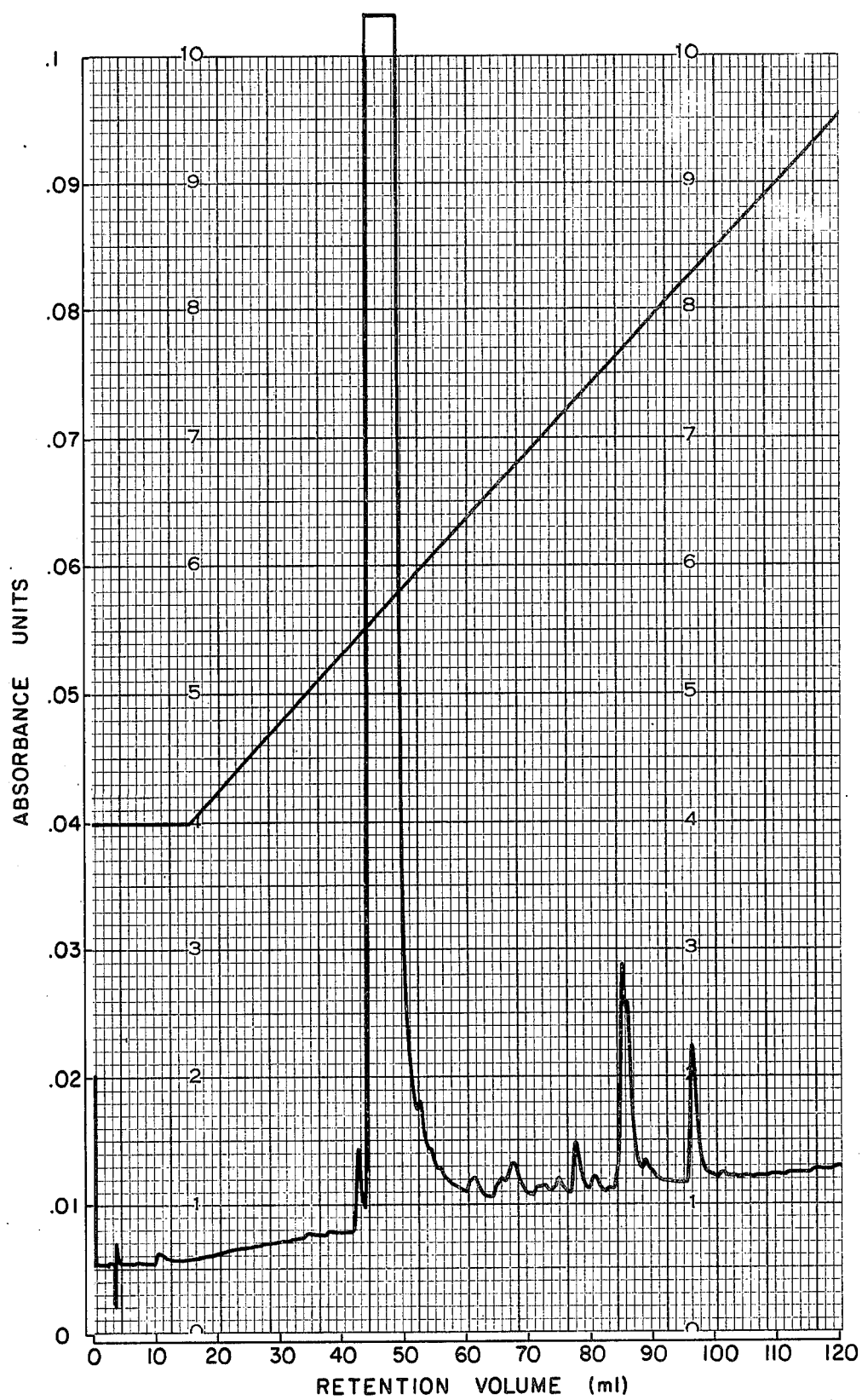

Relative to the practice of the method of the present invention, dichloride purity can be determined in various ways. FIG. 3, for example, is a liquid chromatogram of dichloride made in accordance with the practice of the present invention. It has been found that dichloride capable of providing a liquid chromatogram, such as shown by FIGS. 2 and 3, can be converted to high impact polycarbonate exhibiting a Notched Izod impact value of at least 15 ft-lbs/in. in accordance with ASTM procedure D256 Method A. Liquid chromatograms can be generated with a Waters Model 244 liquid chromatograph, equipped with a Model U6K injector, a $\mu$Bondapak $C_{18}$ column, a Model 44 detector operated at 280 nm, adjusted to 0.1 absorbance units full scale (AUFS) and a 10 millivolt Houston Instruments Omniscribe recorder with a chart speed of 0.25 centimeters per minute. There is prepared a 10% by weight solution of the dichloride in methanol. A 10 microliter sample solution can be injected into the column and eluted at 2 ml per minute, where the solvent mixture is programmed linearly over a 1 hour period. The composition of the methanol in water eluting solvent can vary from an initial composition of 40% methanol in water by volume to a final composition of 100% methanol. In order to determine whether the dichloride sample is sufficiently pure to make high impact polycarbonate, the liquid chromatograph as described above can be set at 0.1 AUFS. The resulting scan should show a predominant dichloride absorbance and be substantially free of other absorbances which exceed 60% of 0.1 AUFS.

Color is another measure of dichloride purity. The color of the dichloride can be measured on a Carey 14 Recording Spectrophotometer. A solution of 2.5 grams of the dichloride in 50 ml of methanol can be placed in a 10 centimeter cell. There is employed a 425 nm light source. If the dichloride absorbance is less than about 0.3, it is considered substantially color free. It has been found that colored dichloride results in the production of low impact polycarbonate which darkens considerably during or after conventional injection molding procedure. Using the aforementioned color test, the dichloride of FIG. 1 was found to be freater than 2. The dichlorides shown by FIGS. 2 and 3 were found to have an absorbance value of less than 0.3.

Included by the dipolar aprotic solvents which can be used in the practice of the present invention are, for example, dimethylformamide, which is the preferred solvent, as well as dimethylacetamide. N-methylpyrrolidone, dimethyl sulfoxide, etc., and mixtures of such solvents with other solvents, such as toluene, xylene, etc.

Included by the halid free basic alkali metal compounds which can be used in the practice of the method of the present invention are, for example, sodium hydroxide, sodium carbonate, sodium bicarbonate, potassium phosphate, potassium carbonate, potassium bicarbonate, potassium hydroxide, etc.

In the practice of the invention, the trichloride is dissolved in the dipolar aprotic solvent along with the basic alkali metal compound. The order of addition of the various ingredients is not critical. Dehydrochlorination of the trichloride can be effected under an inert atmosphere, such as by using nitrogen, etc.

Dehydrochlorination can be effected at a temperature in the range of from 40° C up to 120° C, and preferably from 70° C to 100° C. There can be utilized from 1 to 2 moles of the basic alkali metal compound. Depending upon the temperature and the amount of basic alkali metal compound used, dehydrochlorination can be effected over a period of from 90 minutes or less up to 45 hours.

Recovery of the dichloride can be achieved by the addition of water and mineral or organic acid followed by allowing the mixture to cool. In instances where the initial dehydrohalogenation temperature is in the range of 40° C to 80° C, it has been found expedient to heat the mixture after addition of water, etc., to allow cooling to proceed from about 70° C to effect separation of dichloride crystals. After drying, the purity of the dichloride is generally sufficient to employ directly to make valuable injection moldable polycarbonates.

In order that those skilled in the art will be better able to practice the invention, the following examples are given by way of illustration and not by way of limitation. All parts are by weight.

EXAMPLE 1

There were charged to a reaction vessel, 1243 parts of sulfuric acid and 689 parts of glacial acetic acid. The resulting mixture was cooled to 27° C. There was added 1190 parts of hot phenol to the mixture which was cooled to 20° C. There was added to the resulting mixture over a 7 hour period, 622 parts of chloral while the temperature of the mixture was maintained between 18°–21° C. After stirring the mixture for 24 hours, there was added 1160 parts of water, resulting in the production of crude reaction product. The product was recovered in a basket centrifuge. After washing with water, there was obtained 1461 parts of solid. Based on method of preparation, the product was the trichloride of formula (2).

The above trichloride is dissolved in isopropanol in a proportion of one part of trichloride to 2.18 parts of isopropanol. The isoporpanol solution is heated to 50° C, and water is added to produce a mixture having 12% by weight solids. The mixture is then cooled to 20° C over a 2 hour period. There is obtained an 82% yield of trichloride crystals which are collected.

A solution of 1816 parts of the above trichloride, 606.3 parts of reagent grade sodium carbonate in about 11,470 parts of dimethylformamide was heated to 75°-80° C. The mixture was stirred while nitrogen was slowly bubbled through the mixture for about 30 hours and then was allowed to cool to room temperature. To the resulting mixture, there was added 16,100 parts water with stirring. The resulting solution exothermed to about 45°-50° C when the water was added and then allowed to cool slowly to room temperature. A solid crystallized from the solution which was collected on a basket centrifuge and washed thoroughly with distilled water. The resulting product was then dried at 80° C for 74 hours in a vacuum oven. There was obtained a 97% yield of the dichloride of formula (1).

The dichloride was filtered through a 0.2 μColumbia filtered pad in 30% methanol solution containing charcoal. Water was added to the filtered solution to make a 15% aqueous methanol solution. This solution was heated to reflux and crystals formed upon cooling. The crystals were collected on a basket centrifuge, washed with water and dried at 80° C for 48 hours. The product was found to be haze-free with an absorbance value of less than 0.3 on a Carey 14 spectrophotometer as previously described.

Following the previously described procedure, a liquid chromatogram was generated by preparing a 10% solution of the crystalline dichloride in methanol. A 10 microliter sample of the solution is injected into the column of a Waters Model 244 liquid chromatograph and eluted at 2 ml per minute. There was obtained the liquid chromatogram shown by FIG. 3.

Phosgene is bubbled at a rate of 0.52 to 1.63 parts per hour into a mixture over a period of 48 minutes consisting of 1 part of the above dichloride, 2.9 to 6.3 parts of water, 4.7 to 9 parts of dichloromethane, 0.008 part of phenol, 0.005 to 0.008 part of triethylamine and 0.002 part of sodium gluconate. During the introduction of the phosgene, the mixture is agitated and maintained at a pH of about 11 to 11.5, employing a 50% aqueous sodium hydroxide solution. The mixture becomes viscous and shows no further build in viscoisty. The mixture is then diluted with 2.9 to 4.3 parts of dichloromethane. The organic layer is separated from the aqueous phase. The organic layer is then washed with a 0.01 N-aqueous hydrochloric acid solution and then with water to produce a neutral resin solution. The product is isolated by precipitation in accordance with the procedure described by Niblett et al, U.S. Pat. No. 3,508,339. There is obtained a polycarbonate having an intrinsic viscosity of about 0.52 dl/g in methylene chloride at 25° C.

Test specimens are prepared from the above polycarbonate to determine its Notched Izod impact value in accordance with ASTM procedure D256 Method A.

The extrusion is done using a ¾ inch Brabender extruder fitted with a general purpose screw (compression ratio, 2:1), having a length/diameter ratio of 15:1. A 15° tip is used along with a ⅛ inch rod die. The temperature is maintained at 530° F over the entire barrel. The screw speed is 100 rpm. The extrudate is cooled and pelletized. The polymer powder is fed to the extruder throat resulting in an extrusion rate of about 3.8 pounds per hour and the torque is 1200 meter/gram.

The pellets of the polymer sample is dried in an air oven at 125° C for 3 hours. The dried pellets are molded on a 0.8 ounce Battenfeld injection molding machine with a screw speed of 80 rpm. The molding conditions are as follows: (1) Temperature—barrel set points, 570° F and mold surface, 200° F. (2) Pressure—injection, 23,000 PSI and back pressure, minimum. (3) Cycle times—injection time/speed, 10 sec/fast; hold time, 15 sec.; open time, 2 sec.

It is found that a Notched Izod impact value of the chloroethylene polycarbonate is 15 ft-lbs/in.

The chloroethylene polycarbonates made in accordance with the practice of the present invention can be injection molded to a variety of useful high impact parts and shapes similar to the molding of Lexan polycarbonate.

Although the above example is directed to only a few of the very many variables which can be used in the practice of the method of the present invention, it should be understood that the present invention can employ a much broader variety of dipolar aprotic solvents as previously indicated in the description preceeding this example, as well as other basic alkali metal compounds to effect the dehydrochlorination of the trichloride of formula (2).

What we claim as new and desire to secure by Letters Patent of the United States is:

1. A method for making the dichloride of the formula,

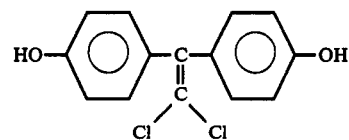

by dehydrochlorinating the trichloride of the formula,

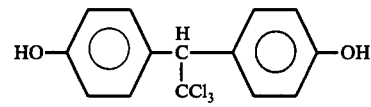

which comprises,
  (1) heating to a temperature in the range of 40° C to 120° C, a mixture containing as essential ingredients,
    (a) the trichloride,
    (b) a dipolar aprotic solvent,
    (c) a basic halide-free alkali metal compound selected from sodium compounds and potassium compounds,
  where, per 100 parts by weight of (b), there is present from 5 to 100 parts of (a), and per mole of (a), there is present at least 1.1 moles or molar equivalents of alkali metal of (c),
  (2) adding water and a member selected from the class consisting of organic acid and mineral acid in amounts sufficient to produce a mixture comprising from 0.8 to 2 parts of water per part of dipolar aprotic solent, (3) effecting the crystallization of dichloride crystals from the mixture of (2) at a temperature of from about 35° C to 120° C, and (4) recovering the crystalline dichloride from the resulting mixture of (3).

2. A method in accordance with claim 1, where the crystalline dichloride recovered from the mixture is further recrystallized 3. A method in accordance with claim 1, where the dipolar aprotic solvent is dimethylformamide.

4. A method in accordance with claim 1, where the dipolar aprotic solvent is dimethylsulfoxide.

5. A method in accordance with claim 1, where the basic alkali metal compound is sodium carbonate.

6. A method in accordance with claim 1, where the basic alkali metal compound is sodium bicarbonate.

7. A method in accordance with claim 1, where the basic alkali metal compound is sodium hydroxide.

8. A method in accordance with claim 1, where the basic alkali metal compound is potassium carbonate.

9. A method in accordance with claim 1, where the basic alkali metal compound is potassium phosphate.

10. A method in accordance with claim 1, where the basic alkali metal compound is potassium bicarbonate.

* * * * *